US012629021B2

(12) United States Patent
Chandrasekaran et al.

(10) Patent No.: US 12,629,021 B2
(45) Date of Patent: May 19, 2026

(54) INFORMATION PROCESSING SYSTEM, INFORMATION PROCESSING METHOD, AND STORAGE MEDIUM FOR EYE GAZE BASED LIVENESS DETECTION

(71) Applicant: NEC Corporation, Tokyo (JP)

(72) Inventors: Arun Chandrasekaran, Sacramento, CA (US); Kris Ranganath, Sacramento, CA (US); Vinoth Babu Amirthalingam, Sacramento, CA (US)

(73) Assignee: NEC CORPORATION, Tokyo (JP)

( * ) Notice: Subject to any disclaimer, the term of this patent is extended or adjusted under 35 U.S.C. 154(b) by 885 days.

(21) Appl. No.: 17/794,006

(22) PCT Filed: Jan. 27, 2021

(86) PCT No.: PCT/JP2021/002734

§ 371 (c)(1),
(2) Date: Jul. 20, 2022

(87) PCT Pub. No.: WO2021/153578

PCT Pub. Date: Aug. 5, 2021

(65) Prior Publication Data

US 2023/0033687 A1 Feb. 2, 2023

Related U.S. Application Data

(60) Provisional application No. 62/966,341, filed on Jan. 27, 2020.

(51) Int. Cl.
*A61B 3/113* (2006.01)
*A61B 3/14* (2006.01)
(Continued)

(52) U.S. Cl.
CPC .............. *A61B 3/113* (2013.01); *A61B 3/145* (2013.01); *G06V 40/197* (2022.01); *G06V 40/40* (2022.01)

(58) Field of Classification Search
CPC ......... A61B 3/113; A61B 3/145; A61B 5/398; A61B 5/163; A61B 3/14; A61B 3/1216;
(Continued)

(56) References Cited

U.S. PATENT DOCUMENTS

2007/0263908 A1 11/2007 Tsukahara
2010/0096300 A1 4/2010 Otto et al.
(Continued)

FOREIGN PATENT DOCUMENTS

JP 2017-142859 A 8/2017
WO 2016/168814 A1 10/2016
WO 2019/023032 A1 1/2019

OTHER PUBLICATIONS

International Search Report for PCT Application No. PCT/JP2021/002734, mailed on Apr. 20, 2021.
(Continued)

*Primary Examiner* — Brandi N Thomas
(74) *Attorney, Agent, or Firm* — Sughrue Mion, PLLC

(57) ABSTRACT

An apparatus includes: a memory storing one or more instructions; and a processor configured to execute the one or more instructions to: obtain a plurality of images, each of the plurality of images including an eye of a subject; obtain a plurality of gaze angles, each of the plurality of gaze angles corresponding to the eye of the user; and detect liveness of the subject based on the plurality of gaze angles.

5 Claims, 6 Drawing Sheets

(51) Int. Cl.
    *G06V 40/18*      (2022.01)
    *G06V 40/40*      (2022.01)

(58) Field of Classification Search
    CPC ........ G02B 27/0172; G02B 2027/0138; G02B
                  2027/0134; G06F 3/013; G06F 3/011;
                                     G16H 50/20
    See application file for complete search history.

(56) References Cited

U.S. PATENT DOCUMENTS

| | | | |
|---|---|---|---|
| 2016/0019410 A1 | 1/2016 | Komogortsev | |
| 2019/0392145 A1* | 12/2019 | Komogortsev | ......... G06F 21/32 |

OTHER PUBLICATIONS

Written opinion for PCT Application No. PCT/JP2021/002734, mailed on Apr. 20, 2021.
Tetsuya Yonezawa et al., "Development of an Eye Gaze Interface System and Improvement of Cursor Control Function", Proceedings of the International Conference on Signal Processing and Multimedia Applications, 2008, XP093048267, 4 pages total.
Communication dated Jun. 1, 2023 issued by the European Patent Office in counterpart European Application No. 21746929.5.

\* cited by examiner

FIG. 1

OBTAIN A PLURALITY OF IMAGES, EACH OF THE PLURALITY OF IMAGES INCLUDING AN EYE OF A SUBJECT — S210

OBTAIN A PLURALITY OF GAZE ANGLES, EACH OF THE PLURALITY OF GAZE ANGLES CORRESPONDING TO THE EYE OF THE USER — S220

DETECT LIVENESS OF THE SUBJECT BASED ON THE PLURALITY OF GAZE ANGLES — S230

Figure 6:
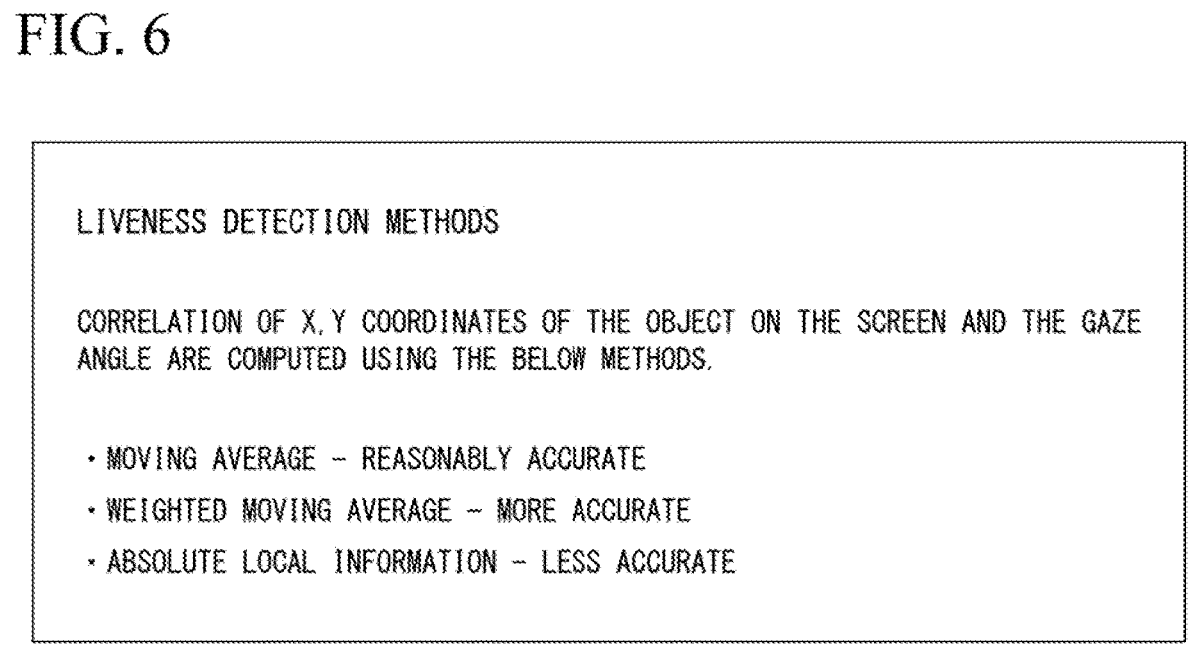

LIVENESS DETECTION METHODS

CORRELATION OF X,Y COORDINATES OF THE OBJECT ON THE SCREEN AND THE GAZE ANGLE ARE COMPUTED USING THE BELOW METHODS.

- MOVING AVERAGE - REASONABLY ACCURATE
- WEIGHTED MOVING AVERAGE - MORE ACCURATE
- ABSOLUTE LOCAL INFORMATION - LESS ACCURATE

INFORMATION PROCESSING SYSTEM, INFORMATION PROCESSING METHOD, AND STORAGE MEDIUM FOR EYE GAZE BASED LIVENESS DETECTION

This application is a National Stage Entry of PCT/JP2021/002734 filed on Jan. 27, 2021, which claims priority from U.S. Provisional Patent Application 62/966,341 filed on Jan. 27, 2020, the contents of all of which are incorporated herein by reference, in their entirety.

TECHNICAL FIELD

The disclosure relates to an information processing system, an information processing method, and a storage medium, more particularly, to an information processing system, an information processing method, and a storage medium for performing eye gaze based liveness detection.

BACKGROUND ART

Conventionally, there exist liveness detection techniques.

SUMMARY

One or more example embodiments of the disclosure may provide an information processing system, an information processing method, and a storage medium for detecting liveness based on eye gaze information of a user.

According to an aspect of the disclosure, there is provided an information processing apparatus comprising: a memory storing one or more instructions; and a processor configured to execute the one or more instructions to: obtain a plurality of images, each of the plurality of images including an eye of a subject; obtain a plurality of gaze angles, each of the plurality of gaze angles corresponding to the eye of the user; and detect liveness of the subject based on the plurality of gaze angles.

The processor may be further configured to: calculate a moving average of the plurality of gaze angles; and detect the liveness of the subject based on the moving average of the plurality of gaze angles.

The processor may be further configured to: identify a pattern of movement of the plurality of gaze angles; and detect the liveness of the subject based on the pattern of movement of the plurality of gaze angles.

The plurality of images may be subsequent frames in a moving image captured by a camera.

The plurality of gaze angles may be determined based on angle of the eye with respect to a reference point.

One or more example embodiments of the disclosure will be described below with reference to the attached drawings.

BRIEF DESCRIPTION OF DRAWINGS

FIG. 1 illustrates a block diagram of a hardware configuration of an information processing device according to an example embodiment.

FIG. 4 is a second additional diagram and shows a moving point on a display screen and a gazed position of a user.

FIG. 6 is a fourth additional diagram and is an explanation diagram of liveness detection methods.

DESCRIPTION OF EXAMPLE EMBODIMENTS

Figure 2:
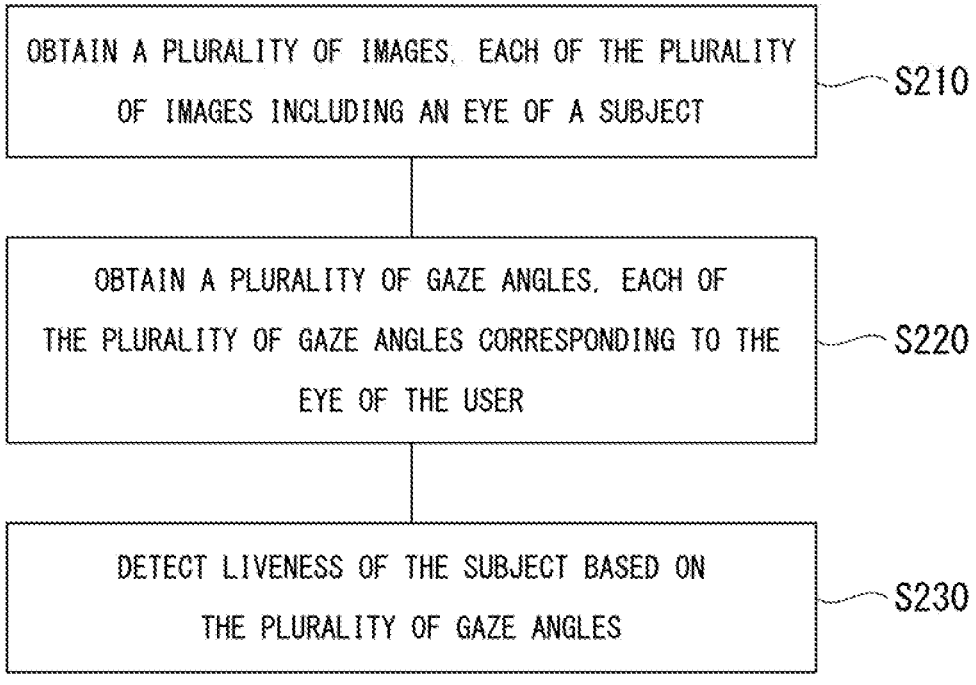
FIG. 2 is a flowchart illustrating the outline of the process performed by the information processing device for detecting a liveness of the user.

According to an example embodiment of the disclosure, an object may be displayed on a display screen at random X, Y coordinate positions at various instances in time and a user is prompted/expected to look at the object on the screen. At this point, the camera situated on the top of the display screen may capture image frames of the user and the position of the eyes and the gaze angle are obtained from the image frames. According to an embodiment of the disclosure, the liveness estimator estimates or detects the eye gaze and effectively correlates it with the X,Y coordinates of the object displayed on the screen to determine if photo or video being processed is a spoof attack or a real live face. Since the object is displayed at random positions on the screen and the correlation of X,Y coordinates with the eye gaze is very high, the photo/video based spoofs can be combatted effectively.

Figure 1:
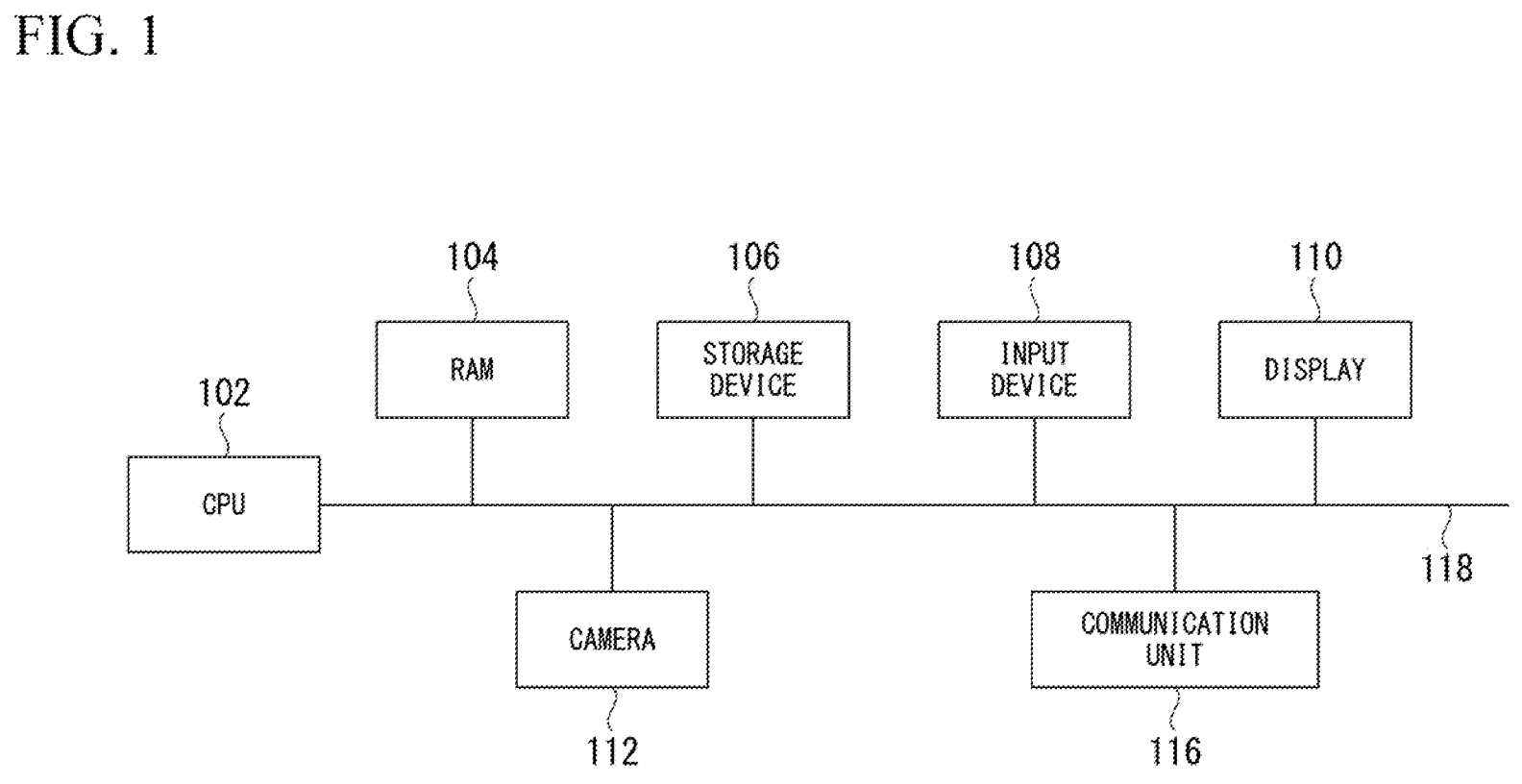

FIG. 1 illustrates a block diagram of a hardware configuration of an information processing device according to an example embodiment. According to an embodiment, the information processing device may be a mobile device (i.e., smart phone, laptops, tablets, etc.) or other electronic devices (i.e., computer). According to an embodiment, the information processing device has a CPU 102, a RAM 104, a storage device 106, an input device 108, a display 110, a camera 112, and a communication unit 116. The CPU 102, the RAM 104, the storage device 106, the input device 108, the display 110, the camera 112, and the communication unit 116 are connected to a bus line 118.

The CPU 102 may function as a control unit that operates by executing a program stored in the storage device 106 and controls the operation of the information processing device. Further, the CPU 102 may execute an application program stored in the storage device 106 to perform various processes as the automated gate apparatus 1. The RAM 104 may provide a memory field necessary for the operation of the CPU 102.

The storage device 106 may be formed of a storage medium such as a non-volatile memory, a hard disk drive, or the like and functions as a storage unit. The storage device 106 may store a program executed by the CPU 102, data referenced by the CPU 102 when the program is executed, or the like.

According to an embodiment, the information processing device may combat photo and video based spoofing by effectively eliminating such attacks and allowing only a real person's face to pass through. This includes biometric terminals at the airport, flight check-in kiosks, e-gates (biometric electronic boarding gates), etc., where airlines applications require passengers to enroll their faces using their mobile phones. By providing a gaze based liveness detection to confirm the liveness of the person using the application, photo and even video based spoofing may be prevented, and thus security is improved.

The camera 112 may capture an image of the user using the application in the device, such as a mobile device and laptops, and other computer devices. For example, the camera 112 may be a digital camera that captures a front area of the mobile device. The image may be captured continuously or periodically. The image may be captured in a plurality of frames as moving images.

The communication unit 116 may be connected to a network and may transmit and receive data via the network.

The communication unit 116 communicates with a server or the like under the control of the CPU 102.

According to an example embodiment, the CPU 102 may obtain the image from the camera 112 and process the image to detect an eye gaze of the user within the image. Here, the CPU 102 may use Artificial Intelligence (AI) and/or machine learning to detect or estimate the eye gaze. For instance, the CPU 102 may perform object detection (i.e., eye detection) using object classification followed by object localization to detect or estimate the eye gaze. According to an embodiment, the eye-gaze detection algorithm may use custom trained Deep Neural Networks (DNN).

According to other example embodiment, methods different than AI and/or machine learning may be used to detect the eye and eye-gaze of the user.

According to an example embodiment, after detecting the eye gaze, the CPU 102 may identify an eye gaze angle. According to an embodiment, the eye gaze angle may be an angle between a focal point of the eye gaze and a reference point. According to an embodiment, the camera may be the reference point. Moreover, the CPU 102 may obtain eye gaze angle in subsequent image frames.

According to an example embodiment, after obtaining the eye gaze angle, a movement pattern of the eye gaze is obtained based on the detected or estimated eye gaze angle in subsequent image frames. According to an embodiment, the movement pattern of the eye gaze may be determined by using ten image frames.

Figure 3:
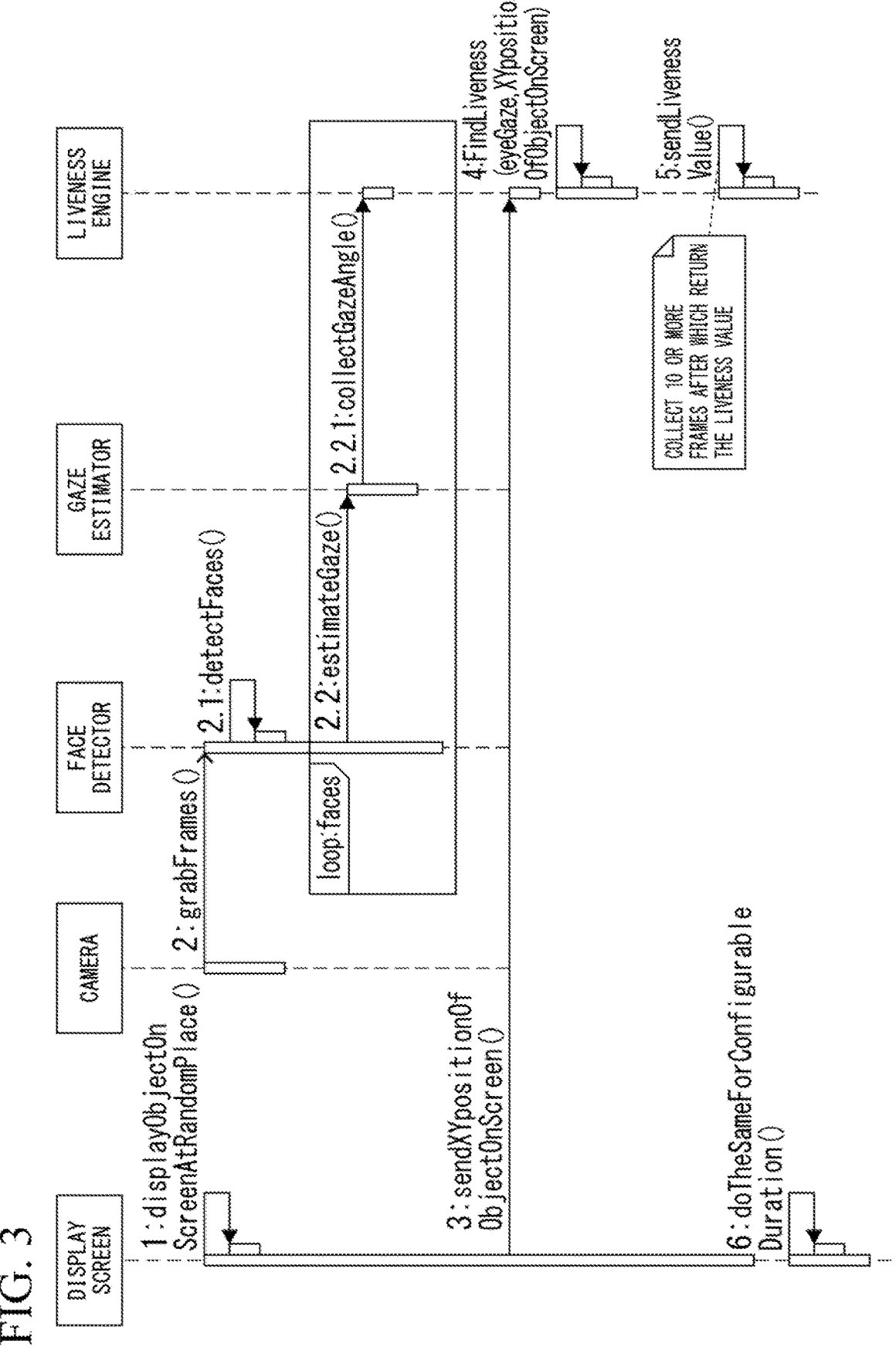
FIG. 3 is a first additional diagram and shows a sequence diagram of an eye gaze based liveness detection.
Figure 4:
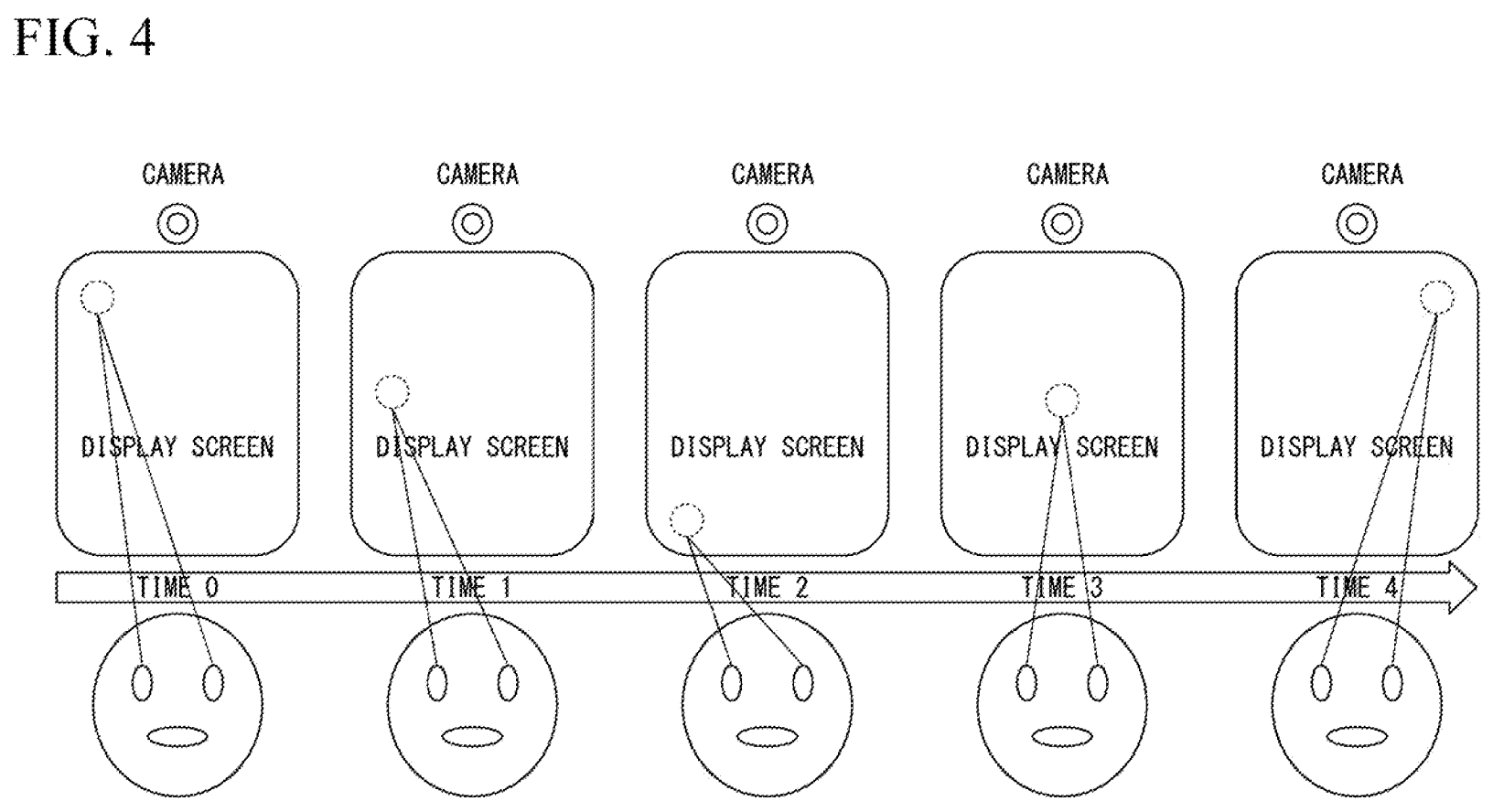
Figure 5:
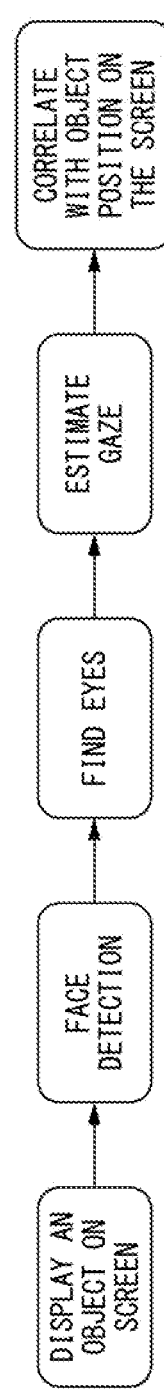
FIG. 5 is a third additional diagram and shows an eye gaze based liveness detection workflow.

According to an example embodiment, the CPU 102 may control the display to display a moving point, icon or image to move in a particular manner on the screen of the display 110 prior to and/or during the detection of the eye gaze. The user may be prompted to look at and follow the displayed moving point, icon or image. See FIGS. 3 to 6. FIG. 3 shows a sequence diagram of an eye gaze based liveness detection. In the sequence, the display screen displays an object on a screen at random place (Step 1). The camera grabs frames (Step 2). The face detector detects faces (Step 2.1). The face detector estimates a gaze (Step 2.2). The gaze estimator collects a gaze angle. The live engine finds liveness based on the eye gaze and the XY position of an object on a screen. FIG. 4 shows a moving point on a display screen and a gazed position of a user at Time 0 to Time 4. FIG. 5 shows an eye gaze based liveness detection workflow. The workflow includes displaying an object on a screen, detecting a face, finding eyes, estimating eye gaze and correlating the eye gaze with an object position on the screen. FIG. 6 is an explanation diagram of liveness detection methods. In the liveness detection methods, correlation of X, Y coordinates of the object on the screen and the gaze angle are computed using the method of using moving average, the method of weighted moving average, or the method of absolute local information. The method of using moving average is reasonably accurate. The method of using weighted moving average is more accurate. The method of using absolute local information is less accurate.

In this manner, the CPU 102 may compare the moving pattern of the eye gaze angle with a moving pattern of the moving point/icon/image on the screen and determine whether the moving pattern of the eye gaze angle coincides with the moving pattern of the moving point/icon/image. In a case in which the moving pattern of the eye gaze angle coincides with the moving pattern of the moving point/icon/image within a particular degree, the CPU 102 may determine that the user is live.

On the other hand, in a case in which the moving pattern of the eye gaze angle does not coincide with the moving pattern of the moving point/icon/image within the particular degree, the CPU 102 may determine that the user is not live.

According to another embodiment, the CPU 102 may calculate a moving average of the plurality of gaze angles and detect the liveness of the subject based on the moving average of the plurality of gaze angles. For instance, the CPU 102 may determine whether the moving average of the plurality of gaze angles for a specified number of frames matches a moving average of the moving pattern of the moving point/icon/image corresponding to the specified number of frames.

In a case in which the moving average of the eye gaze angle coincides with the moving average of the moving point/icon/image within a particular threshold value, the CPU 102 may determine that the user is live.

On the other hand, in a case in which the moving average of the eye gaze angle does not coincide with the moving average of the moving point/icon/image within a particular threshold value, the CPU 102 may determine that the user is not live.

FIG. 2 is a flowchart illustrating the outline of the process performed by the information processing device for detecting a liveness of the user.

In S210, the CPU 102 may obtain a plurality of images, each of the plurality of images including an eye of a subject. According to an example embodiment, the plurality of images may be an image of the environment in front of a mobile device or a computer.

In S220, the CPU 102 may obtain a plurality of gaze angles, each of the plurality of gaze angles corresponding to the eye of the user. In order to obtain the plurality of gaze angles, the CPU 102 may obtain the image from the camera 112 and process the image to detect an eye gaze of the user within the image. Here, the CPU 102 may use Artificial Intelligence (AI) and/or machine learning to detect or estimate the eye gaze. For instance, the CPU 102 may perform object detection (i.e., eye detection) using object classification followed by object localization to detect or estimate the eye gaze. According to an embodiment, the eye-gaze detection algorithm may use custom trained Deep Neural Networks (DNN).

In S230, the CPU 102 may detect liveness of the subject based on the plurality of gaze angles. For instance, the CPU 102 may detect the liveness based on the moving pattern and/or the moving average of the eye gaze angle, i.e., whether it coincides with the moving pattern and/or average of the moving point/icon/image. According to another example embodiment, the CPU 102 may use weighted moving average of the moving point/icon/image. According to yet another embodiment, the CPU 102 may use absolute local information, which may correlate the gaze angle with the location of the object on the screen in a point by point basis. For instance, the CPU 102 may determine if a first gaze angle coincides with a first position of the object on the screen and determine if a second gaze angle coincides with a second position of the object on the screen.

While the information processing apparatus and systems used in liveness detection for airport applications have been illustrated as examples in each of the above example embodiments, the disclosure is also applicable to areas of liveness detection by appropriately changing the configuration of the one or more example embodiments.

The scope of one or more example embodiments also includes a processing method of storing, in a storage medium, a program that causes the configuration of the example embodiment to operate to implement the function of the example embodiment described above, reading out as a code the program stored in the storage medium, and executing the code in a computer. That is, a computer readable storage medium is also included in the scope of each example embodiment. Further, not only the storage medium in which the program described above is stored but also the program itself is included in each example embodiment. Further, one or more components included in the example embodiments described above may be a circuit such as an Application Specific Integrated Circuit (ASIC), a Field Programmable Gate Array (FPGA), or the like configured to implement the function of each component.

As the storage medium, for example, a floppy (registered trademark) disk, a hard disk, an optical disk, a magneto-optical disk, a Compact Disk (CD)-ROM, a magnetic tape, a nonvolatile memory card, or a ROM can be used. Further, the scope of each of the example embodiments includes an example that operates on Operating System (OS) to perform a process in cooperation with another software or a function of an add-in board without being limited to an example that performs a process by an individual program stored in the storage medium.

The service implemented by the function of one or more example embodiments described above can be provided to the user in a form of Software as a Service (SaaS).

Note that all the example embodiments described above are mere examples of embodiments in implementing the disclosure, and the technical scope of the disclosure should not be construed in a limiting sense by these example embodiments. That is, the disclosure can be implemented in various forms without departing from the technical concept thereof or the primary feature thereof.

This application is based upon and claims the benefit of priority from U.S. provisional patent application No. 62/966,341, filed Jan. 27, 2020, the disclosure of which is incorporated herein in its entirety.

What is claimed is:

1. An apparatus comprising:

a memory storing one or more instructions; and a processor configured to execute the one or more instructions to:

obtain a plurality of images, which are subsequent frames in a moving image captured by a camera, each of the plurality of images including an eye of a subject;

obtain a plurality of gaze angles, each of the plurality of gaze angles corresponding to the eye of the subject;

calculate a moving average of the plurality of gaze angles;

identify a pattern of movement of the plurality of gaze angles; and detect liveness of the subject in a case in which the moving average of the plurality of gaze angles for a specified number of frames out of the frames coincides with a moving average of the moving pattern of the position of the moving object on the display screen corresponding to the specified number of frames within a particular threshold value.

2. The apparatus of claim 1, wherein the plurality of gaze angles are determined based on angle of the eye with respect to a reference point.

3. The apparatus of claim 1, wherein the processor is further configured to:

display the moving object on the display screen to prompt the subject to follow the moving object;

compare a moving pattern of the gaze angles with a pattern of the moving object; and detect the liveness of the subject based on a result of the comparison between the pattern of movement of the plurality of gaze angles and the pattern of the moving object.

4. A method comprising:

obtaining a plurality of images, which are subsequent frames in a moving image captured by a camera, each of the plurality of images including an eye of a subject;

obtaining a plurality of gaze angles, each of the plurality of gaze angles corresponding to the eye of the subject;

calculating a moving average of the plurality of gaze angles;

identifying a pattern of movement of the plurality of gaze angles; and detecting liveness of the subject in a case in which the moving average of the plurality of gaze angles for a specified number of frames out of the frames coincides with a moving average of the moving pattern of the position of the moving object on the display screen corresponding to the specified number of frames within a particular threshold value.

5. A non-transitory storage medium storing a program which causes a computer to execute:

obtaining a plurality of images, which are subsequent frames in a moving image captured by a camera, each of the plurality of images including an eye of a subject;

obtaining a plurality of gaze angles, each of the plurality of gaze angles corresponding to the eye of the subject;

calculating a moving average of the plurality of gaze angles;

identifying a pattern of movement of the plurality of gaze angles; and detecting liveness of the subject in a case in which the moving average of the plurality of gaze angles for a specified number of frames out of the frames coincides with a moving average of the moving pattern of the position of the moving object on the display screen corresponding to the specified number of frames within a particular threshold value.

* * * * *